(12) United States Patent
Maes et al.

(10) Patent No.: US 10,780,081 B2
(45) Date of Patent: Sep. 22, 2020

(54) METHOD OF TREATING MULTIPLE SCLEROSIS EMPLOYING A LSD1-INHIBITOR

(71) Applicant: ORYZON GENOMICS, S.A., Madrid (ES)

(72) Inventors: Tamara Maes, Cornellà de Llobregat (ES); Cristina Mascaró Crusat, Cornellà de Llobregat (ES); David Rotllant Pozo, Cornellà de Llobregat (ES)

(73) Assignee: Oryzon Genomics, S.A., Madrid (ES)

( * ) Notice: Subject to any disclaimer, the term of this patent is extended or adjusted under 35 U.S.C. 154(b) by 0 days.

(21) Appl. No.: 15/741,871

(22) PCT Filed: Jun. 9, 2017

(86) PCT No.: PCT/EP2017/064206
§ 371 (c)(1),
(2) Date: Jan. 4, 2018

(87) PCT Pub. No.: WO2017/212061
PCT Pub. Date: Dec. 14, 2017

(65) Prior Publication Data
US 2019/0083469 A1    Mar. 21, 2019

(30) Foreign Application Priority Data
Jun. 10, 2016 (WO) ................ PCT/EP2016/063368

(51) Int. Cl.
*A61K 31/4245* (2006.01)
*A61P 25/28* (2006.01)
*A61K 31/42* (2006.01)

(52) U.S. Cl.
CPC .......... *A61K 31/4245* (2013.01); *A61K 31/42* (2013.01); *A61P 25/28* (2018.01)

(58) Field of Classification Search
USPC ........................................................ 514/364
See application file for complete search history.

(56) References Cited

U.S. PATENT DOCUMENTS

| | | |
|---|---|---|
| 4,522,811 A | 6/1985 | Eppstein et al. |
| 8,524,717 B2 | 9/2013 | Guibourt et al. |
| 8,722,743 B2 | 5/2014 | Ortega-Muñoz et al. |
| 8,859,555 B2 | 10/2014 | Ortega-Muñoz et al. |
| 8,946,296 B2 | 2/2015 | Ortega Muñoz et al. |
| 8,993,808 B2 | 3/2015 | Guibourt et al. |
| 9,006,449 B2 | 4/2015 | Fyfe et al. |
| 9,061,966 B2 | 6/2015 | Castro-Palomino Laira et al. |
| 9,149,447 B2 | 10/2015 | Ortega-Muñoz et al. |
| 9,181,198 B2 | 11/2015 | Ortega-Muñoz et al. |
| 9,186,337 B2 | 11/2015 | Baker et al. |
| 9,469,597 B2 | 10/2016 | Ortega Muñoz et al. |
| 9,487,512 B2 | 11/2016 | Ortega Muñoz et al. |
| 9,616,058 B2 | 4/2017 | Castro Palomino Laria et al. |
| 9,670,136 B2 | 6/2017 | Ortega-Muñoz et al. |
| 9,676,701 B2 | 6/2017 | Fyfe et al. |
| 9,708,309 B2 | 7/2017 | Ortega-Muñoz et al. |
| 9,790,196 B2 | 10/2017 | Baker et al. |
| 9,908,859 B2 | 3/2018 | Baker et al. |
| 9,944,601 B2 | 4/2018 | Ortega-Muñoz et al. |
| 2008/0139665 A1 | 6/2008 | Schuele et al. |
| 2010/0324147 A1 | 12/2010 | McCafferty et al. |
| 2014/0296255 A1 | 10/2014 | Maes et al. |
| 2014/0329833 A1 | 11/2014 | Maes et al. |
| 2015/0368186 A1 | 12/2015 | Ortega Muñoz et al. |
| 2016/0000768 A1 | 1/2016 | Castro-Palomino Laria et al. |
| 2016/0045456 A1 | 2/2016 | Guibourt et al. |
| 2016/0081947 A1 | 3/2016 | Maes et al. |
| 2017/0209432 A1 | 7/2017 | Fyfe et al. |
| 2017/0281566 A1 | 10/2017 | Ciceri et al. |
| 2017/0281567 A1 | 10/2017 | Demario et al. |
| 2018/0079709 A1 | 3/2018 | Ortega Muñoz et al. |
| 2018/0086692 A1 | 3/2018 | Diodone et al. |
| 2018/0127406 A1 | 5/2018 | Ortega-Muñoz et al. |
| 2018/0284095 A1 | 10/2018 | Maes et al. |

FOREIGN PATENT DOCUMENTS

| | | |
|---|---|---|
| EP | 1704859 | 9/2006 |
| EP | 2 258 865 A1 | 12/2010 |
| WO | WO2006/071608 | 7/2006 |
| WO | WO2006/087206 | 8/2006 |
| WO | WO2007/021839 | 7/2007 |
| WO | WO2008/127734 | 10/2008 |
| WO | WO2010/011845 | 1/2010 |
| WO | WO2010/043721 | 4/2010 |
| WO | WO2010/084160 | 7/2010 |
| WO | WO2010/139784 | 12/2010 |
| WO | WO2010/143582 | 12/2010 |

(Continued)

OTHER PUBLICATIONS

Lassmann (Mechanism of neurodeneration shared between multiple sclerosis and Alzheimer's disease, Journal Neural Transm, 2011, 118, pp. 747-752).*

Fitzner (Chronic Progressive Multiple Sclerosis—Pathogenesis of Neurodegeneration and Therapeutic Streategies, Current Neuropharmacology, 2010, 8, pp. 305-315).*

Buesa, Carlos et al., "The Dual LSD1-MAOB Inhibitor Ory2001 Prevents the Development of the Memory Deficit in SAMP8 Mice Through Induction of Neuronal Plasticity and Reduction of Neuroinflammation," Alzheimer's & Dementia: The Journal of the Alzheimer's Association, vol. 11, No. 7 (2015).

Friedman, Lauren G., "Meeting report on the Alzheimer's Drug Discovery Foundation 14th International Conference on Alzheimer's Drug Discovery," Alzheimer's Research & Therapy, vol. 6, No. 2, p. 22 (2014).

(Continued)

*Primary Examiner* — Kathrien A Cruz
(74) *Attorney, Agent, or Firm* — Finnegan, Henderson, Farabow, Garrett & Dunner, LLP

(57) ABSTRACT

Provided herein are methods for treating multiple sclerosis using (−) 5-((((trans)-2-(4-(benzyloxy)phenyl)cyclopropyl)amino)methyl)-1,3,4-oxadiazol-2-amine, or a pharmaceutically acceptable salt or solvate thereof.

19 Claims, 10 Drawing Sheets

(56) References Cited

FOREIGN PATENT DOCUMENTS

| WO | WO2011/022489 | 2/2011 |
|---|---|---|
| WO | WO2011/035941 | 3/2011 |
| WO | WO2011/042217 | 4/2011 |
| WO | WO2011/106105 | 9/2011 |
| WO | WO2011/106106 | 9/2011 |
| WO | WO2011/113005 | 9/2011 |
| WO | WO2011/131576 | 10/2011 |
| WO | WO2011/131697 | 10/2011 |
| WO | WO2012/013727 | 2/2012 |
| WO | WO 2012/013728 A1 | 2/2012 |
| WO | WO2012/034116 | 3/2012 |
| WO | WO2012/042042 | 4/2012 |
| WO | WO2012/045883 | 4/2012 |
| WO | WO2012/072713 | 6/2012 |
| WO | WO2012/107498 | 8/2012 |
| WO | WO2012/107499 | 8/2012 |
| WO | WO2012/135113 | 10/2012 |
| WO | WO2012/156531 | 11/2012 |
| WO | WO2012/156537 | 11/2012 |
| WO | WO2013/057320 | 4/2013 |
| WO | WO2013/057322 | 4/2013 |
| WO | WO2016/177656 | 11/2016 |
| WO | WO2016/198649 | 12/2016 |
| WO | WO2017/013061 | 1/2017 |
| WO | WO2017/060319 | 4/2017 |
| WO | WO2017/157813 | 9/2017 |
| WO | WO2017/157825 | 9/2017 |
| WO | WO2017/158136 | 9/2017 |
| WO | WO2018/083138 | 5/2018 |
| WO | WO2018/083189 | 5/2018 |

OTHER PUBLICATIONS

Oryzon, "Oryzon presented new preclinical data of ORY-2001 therapeutic activity in Multiple Sclerosis at CTRIMS-2017," Press Release 2017.
Scoumanne, Ariane et al., "The Lysine-specific Demethylase 1 is Required for Cell Proliferation in Both p53-dependent and-independent Manners," Journal of Biological Chemistry, vol. 282, No. 21, pp. 15471-15475 (2007).
International Search Report for International Application No. PCT/EP2017/064206, dated Sep. 21, 2017.
Written Opinion of the International Searching Authority for International Application No. PCT/EP2017/064206.
Barlesi et al, "Global histone modifications predict prognosis of resected non small-cell lung cancer",J Clin Oncol,2007,25, 4358-4364.
Benelkebir et al, "Enantioselective synthesis of tranylcypromine analogues as lysine demethylase (LSD1) inhibitors", Bioorg Med Chem, 2011,19(12),3709-3716.
Binda et al, "Biochemical, structural, and biological evaluation of tranylcypromine derivatives as inhibitors of histone demethylases LSD1 and LSD2", J Am Chem Soc,2010,132(19),6827-6833.
Brown et al "Transdermal delivery of drugs", Ann. Rev. Med. 1988, 39:221-229.
Burnham "Polymers for delivering peptides and proteins". Am. J. Hosp. Pharm., 1994, 51:210-218.
Choi et al "Histone demethylase LSD1 is required to induce skeletal muscle differentiation by regulating myogenic factors" (2010) Biochemical and Biophysical Research Communications 401(3), 327-332.
Culhane et al, "A mechanism-based inactivator for histone demethylase LSD1", J Am Chem Soc, 2006, 128(14), 4536-4537.
Culhane et al, "Comparative analysis of small molecules and histone substrate analogues as LSD1 lysine demethylase inhibitors", J Am Chem Soc, 2010,132(9),3164-3176.
Di Stefano et al, Mutation of *Drosophila* Lsd1 disrupts H3-K4 methylation, resulting in tissue-specific defects during development, Curr Biol,2007, 17(9), 808-12.
Elsheikh et al "Global histone modifications in breast cancer correlate with tumor phenotypes, prognostic factors and patient outcome", Canc Res, 2009,69, 3802-3809.
Fischer et al, "Recovery of learning and memory is associated with chromatin remodelling", Nature, 2007,447, 178-182.
Forneris et al "LSD1: oxidative chemistry for multifaceted functions in chromatin Regulation." Trends in Biochemical Sciences 2008,33(4), 181-189.
Gooden et al, "Facile synthesis of substituted trans-2-arylcyclopropylamine inhibitors of the human histone demethylase LSD1 and monoamine oxidases A and B", Bioorg Med Chem Lett 2008, 18(10), 3047-51.
Hayami et al, "Overexpression of LSD1 contributes to human carcinogenesis through chromatin regulation in various cancers", Int J Cancer, 2011, 128(3), 574-86.
Huang et al, "Novel oligoamine analogues inhibit lysine-specific demethylase 1 (LSD1) and induce re-expression of epigeneticall silenced genes",Clin Cancer Res,2009, 15(23), 7217-28.
Huang et al, "p53 is regulated by the lysine demethylase LSD1",Nature,2007,449, 105-108.
Huang et al,"Inhibition of lysine-specific demethylase 1 by polyamine analogues results in reexpression of aberrantly silenced genes", PNAS,2007, 104(19), 8023-8028.
Kahl et al, Androgen receptor coactivators lysine-specific histone demethylase 1 and four and a half LIM domain protein 2 predict risk of prostate cancer recurrence, Cancer Res,2006,66 (23), 11341-11347.
Lan et al "Mechanisms involved in the regulation of histone lysine demethylases". Current Opinion in Cell Biology, 2008,20, 316-325.
Lee et al, "Histone H3 lysine 4 demethylation is a target of nonselective antidepressive medications",Chem Biol, 2006,13(6), 563-567.
Liang et al, "Inhibition of the histone demethylase LSD1 blocks alpha-herpesvirus lytic replication and reactivation from latency",Nat Med, 2009,15 (11), 1312-1317.
Lim et al, "Lysine-specific demethylase 1 (LSD1) is highly expressed in ER-negative breast cancers and a biomarker predicting aggressive biology", Carcinogenesis,2010, 31(3), 512-20.
Metzger et al, "LSD1 demethylates repressive histone marks to promote androgen-receptor-dependent transcription",Nature,2005, 437(7057),436-9.
Mimasu et al "Crystal structure of histone demethylase LSD1 and tranylcypromine at 2.25 Å" Biochemical and Biophysical Research Communications ,2008,366, 15-22.
Mimasu et al, "Structurally designed trans-2-phenylcyclopropylamine derivatives potently inhibit histone demethylase LSD1/KDM1", Biochemistry,2010,49(30), 6494-6503.
Neelamegan et al, "Brain-penetrant LSD1 inhibitors can block memory consolidation", ACS Chem Neurosci, 2012, 3(2), 120-128.
Ogasawara et al, "Synthesis and biological activity of optically active NCL-1, a lysine-specific demethylase 1 selective inhibitor",Bioorg Med Chem, 2011, doi:10.1016/j.bmc.2010.12.024.
Phillips et al, "Sustained-release characteristics of a new implantable formulation of disulfiram". J Pharmaceut. Sci., 1984, 73(12):1718-1720.
Pollock et al, Lysine-specific histone demethylase 1 inhibitors control breast cancer proliferation in ERalpha-dependent and-independent manners, ACS Chem Biol 2012,7,1221-1231.
Reddy et al, "Role of lysine-specific demethylase 1 in the proinflammatory phenotype of vascular smooth muscle cells of diabetic mice",Circ Res,2008,103, 615-23.
Schmidt et al,"trans-2-phenylcyclopropylamine is a mechanism-based inactivator of the histone demethylase LSD1", Biochemistry, 2007,46(14),4408-4416.
Schulte et al, "Lysine-specific demethylase 1 is strongly expressed in poorly differentiated neuroblastoma: implications for therapy", Cancer Res,2009,69(5),2065-71.
Scoumanne et al "Protein methylation: a new mechanism of p53 tumor suppressor regulation" Histol Histopathol 2008,23, 1143-1149.
Seligson et al, "Global histone modification patterns predict risk of prostate cancer recurrence",Nature, 2005,435, 1262-1266.
Seligson et al,"Global levels of histone modifications predict prognosis in different cancers",Am J Path, 2009,174,1619-28.

(56) References Cited

OTHER PUBLICATIONS

Sharma et al, "(Bis)urea and (bis)thiourea inhibitors of lysine-specific demethylase 1 as epigenetic modulators", J Med Chem, 2010,53(14), 5197-5212.

Shi et al,"Histone demethylation mediated by the nuclear amine oxidase homolog LSD1", Cell, 2004,119,941-953.

Shi, "Histone lysine demethylases: emerging roles in development, physiology and disease", Nature Reviews Genetics 2007, 8:829-833.

Szewczuk et al, "Mechanistic analysis of a suicide inactivator of histone demethylase LSD1", Biochemistry, 2007,46, 6892-6902.

Ueda et al, "Identification of cell-active lysine specific demethylase 1-selective inhibitors",J Am Chem Soc, 2009,131(48), 17536-17537.

Wang et al, "Novel histone demethylase LSD1 inhibitors selectively target cancer cells with pluripotent stem cell properties," Cancer Research, 2011, 71(23):7238-49.

Wang et al "LSD1 Is a Subunit of the NuRD Complex and Targets the Metastasis Programs in Breast Cancer" Cell 2009, 138, 660-672.

Wang et al, "The lysine demethylase LSD1 (KDM1) is required for maintenance of global DNA methylation", Nature Genetics, 2009, 41(1), 125-129.

Wilson et al, "Disulfiram implantation: a dose response trial". J. Clin. Psychiatry, 1984, 45(6):242-247.

Yang et al "Structural Basis for the Inhibition of the LSD1 Histone Demethylase by the Antidepressant trans-2-Phenylcyclopropylamine" Biochemistry 2007,46 (27), 8058-8065.

Yang et al "Structural basis of histone demethylation by LSD1 revealed by suicide inactivation" Nature Structural & Molecular Biology 2007, 14(6), 535-539.

Johnson et al, CAPLUS, Document No. 157:576967, "Preparation of cyclopropylamines as LSD1 inhibitors in the treatment of cancer", 2012.

Co-pending U.S. Appl. No. 14/843,095, filed Sep. 2, 2015.
Co-pending U.S. Appl. No. 15/458,640, filed Mar. 14, 2017.
Co-pending U.S. Appl. No. 15/497,556, filed Apr. 26, 2017.
Co-pending U.S. Appl. No. 15/623,866, filed Jun. 15, 2017.
Co-pending U.S. Appl. No. 15/571,945, filed Nov. 6, 2017.
Co-pending U.S. Appl. No. 15/735,377, filed Dec. 11, 2017.
Co-pending U.S. Appl. No. 15/766,086, filed Apr. 5, 2018.
Co-pending U.S. Appl. No. 15/911,535, filed Mar. 5, 2018.
Co-pending U.S. Appl. No. 15/988,274, filed May 24, 2018.
Co-pending U.S. Appl. No. 16/042,110, filed Jul. 23, 2018.
Co-pending U.S. Appl. No. 16/084,683, filed Sep. 13, 2018.
Co-pending U.S. Appl. No. 16/084,693, filed Sep. 13, 2018.
Co-pending U.S. Appl. No. 16/085,024, filed Sep. 14, 2018.

\* cited by examiner

A

Cervical Sections

Vehicle          Comp. 1

B

Lumbar Sections

Vehicle          Comp. 1

METHOD OF TREATING MULTIPLE SCLEROSIS EMPLOYING A LSD1-INHIBITOR

This application is a national stage filing under 35 U.S.C. § 371 of International Application No. PCT/EP2017/064206, filed on Jun. 9, 2017, which claims priority of International Application No. PCT/EP2016/063368, filed on Jun. 10, 2016. The contents of these applications are each incorporated herein by reference.

FIELD

The present invention relates generally to the field of multiple sclerosis treatment.

BACKGROUND

Multiple sclerosis (MS) is a chronic, immune-mediated demyelinating disease of the central nervous system (CNS). The immune system attacks the myelin coating around the nerves in the CNS and the nerve fibers themselves. MS is the most common autoimmune disorder affecting the CNS and is a leading cause of disability in young adults. The disease usually begins between the ages of 20 and 50. In 2015, about 2.3 million people were affected worldwide.

MS takes several forms, either with new symptoms occurring in isolated attacks (relapsing forms) or with the disease gradually progressing over time without typical relapses (progressive forms). Progressive forms include primary progressive MS and secondary progressive MS.

Despite intensive investigation, the mechanisms of disease pathogenesis remain unclear, and while there are a number of drugs approved by the FDA for MS, there is still no cure. Among these drugs, most are approved for the treatment of relapse-remitting MS, while there is only one drug approved by the FDA for the treatment of primary progressive MS. Current medications used to treat MS, either relapse-remitting or progressive forms, while modestly effective, can have serious side effects or be poorly tolerated. In addition, many of these drugs must be administered via parenteral route, which is a disadvantage for patients in the context of a chronic disease like MS.

Thus, there is a need for new drugs to treat MS, particularly for drugs that may be also effective against the progressive forms of the disease and/or that exhibit less side effects than current treatments, and which can be administered by the oral route. The present invention addresses these and other needs.

SUMMARY OF THE INVENTION

The invention provides novel methods for treating multiple sclerosis by using (−) 5-((((trans)-2-(4-(benzyloxy)phenyl)cyclopropyl)amino)methyl)-1,3,4-oxadiazol-2-amine, or a pharmaceutically acceptable salt or solvate thereof.

Thus, the present invention provides (−) 5-((((trans)-2-(4-(benzyloxy)phenyl)cyclopropyl)amino)methyl)-1,3,4-oxadiazol-2-amine or a pharmaceutically acceptable salt or solvate thereof for use in the treatment of multiple sclerosis.

The present invention further provides a method for treating multiple sclerosis in a patient (preferably a human), comprising administering to the patient a therapeutically effective amount of (−) 5-((((trans)-2-(4-(benzyloxy)phenyl)cyclopropyl)amino)methyl)-1,3,4-oxadiazol-2-amine or a pharmaceutically acceptable salt or solvate thereof.

The present invention further provides the use of (−) 5-((((trans)-2-(4-(benzyloxy)phenyl)cyclopropyl)amino)methyl)-1,3,4-oxadiazol-2-amine or a pharmaceutically acceptable salt or solvate thereof for the manufacture of a medicament for the treatment of multiple sclerosis.

The present invention further provides the use of (−) 5-((((trans)-2-(4-(benzyloxy)phenyl)cyclopropyl)amino)methyl)-1,3,4-oxadiazol-2-amine or a pharmaceutically acceptable salt or solvate thereof for the treatment of multiple sclerosis.

In some embodiments, the multiple sclerosis is chronic progressive multiple sclerosis, particularly primary progressive multiple sclerosis or secondary progressive multiple sclerosis.

BRIEF DESCRIPTION OF THE DRAWINGS

FIG. 8 shows the levels of several cytokines and chemokines determined by ELISA in spinal cords collected at day 26 post immunization from animals treated with Compound 1 at 0.5 mg/kg p.o. or vehicle according to Example 4.

DETAILED DESCRIPTION OF THE INVENTION

Figure 1:
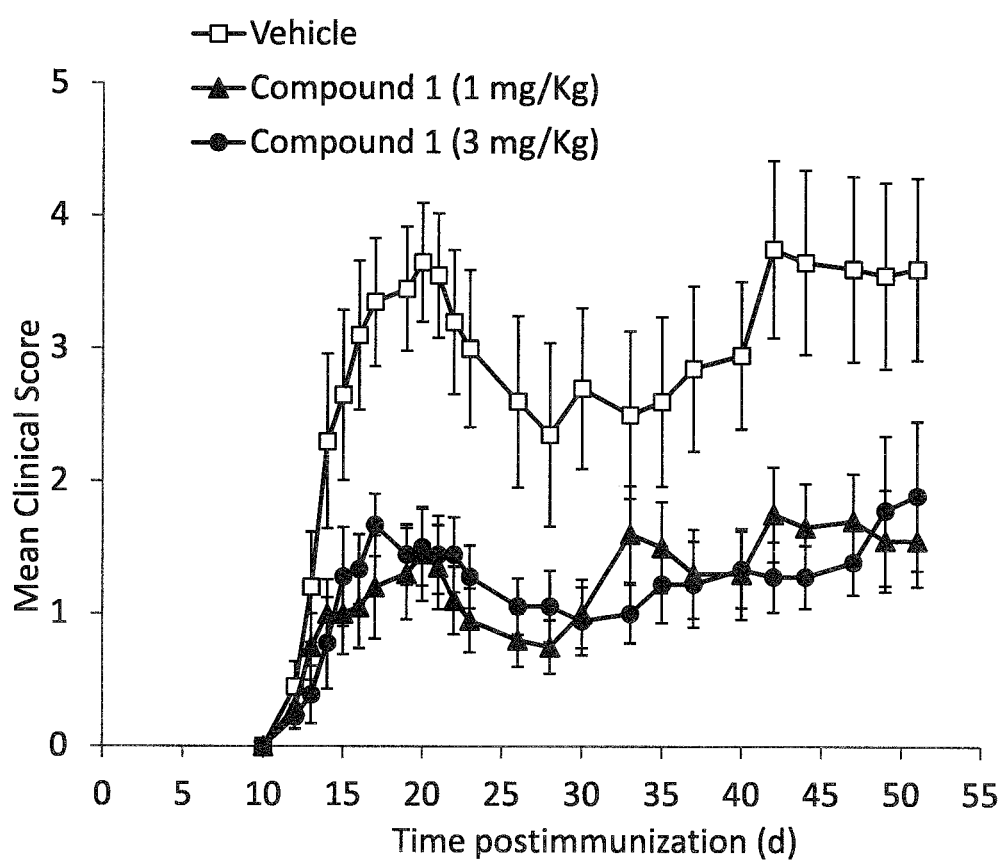
FIG. 1 shows the results obtained with Compound 1 at 1 and 3 mg/kg p.o. in the murine experimental autoimmune encephalomyelitis (EAE) model as described in Example 3.1 and 3.2. Data represent the progression of the disease for each group measured as the mean clinical score (±SEM).

The present invention is based on the identification of the compound (−) 5-((((trans)-2-(4-(benzyloxy)phenyl)cyclopropyl)amino)methyl)-1,3,4-oxadiazol-2-amine as a highly effective therapeutic agent for the treatment of multiple sclerosis, as explained in more detail herein below and illustrated in the Examples. This compound, (−) 5-((((trans)-2-(4-(benzyloxy)phenyl)cyclopropyl)amino)methyl)-1,3,4-oxadiazol-2-amine, is designated in the Examples and Figures as Compound 1 (or Comp. 1). The names "(−) 5-((((trans)-2-(4-(benzyloxy)phenyl)cyclopropyl)amino)methyl)-1,3,4-oxadiazol-2-amine", "Compound 1" or "Comp. 1" are used herein interchangeably.

Accordingly, the present invention provides (−) 5-((((trans)-2-(4-(benzyloxy)phenyl)cyclopropyl)amino)methyl)-1,3,4-oxadiazol-2-amine or a pharmaceutically acceptable salt or solvate thereof for use in the treatment of multiple sclerosis.

The present invention further provides a method for treating multiple sclerosis in a patient (preferably a human), comprising administering to the patient a therapeutically effective amount of (−) 5-((((trans)-2-(4-(benzyloxy)phenyl)cyclopropyl)amino)methyl)-1,3,4-oxadiazol-2-amine or a pharmaceutically acceptable salt or solvate thereof.

The present invention further provides the use of (−) 5-((((trans)-2-(4-(benzyloxy)phenyl)cyclopropyl)amino)methyl)-1,3,4-oxadiazol-2-amine or a pharmaceutically acceptable salt or solvate thereof for the manufacture of a medicament for the treatment of multiple sclerosis.

The present invention further provides the use of (−) 5-((((trans)-2-(4-(benzyloxy)phenyl)cyclopropyl)amino)methyl)-1,3,4-oxadiazol-2-amine or a pharmaceutically acceptable salt or solvate thereof for the treatment of multiple sclerosis.

In some embodiments, the multiple sclerosis is chronic progressive multiple sclerosis (e.g., primary progressive multiple sclerosis or secondary progressive multiple sclerosis).

Accordingly, the present invention further provides (−) 5-((((trans)-2-(4-(benzyloxy)phenyl)cyclopropyl)amino)methyl)-1,3,4-oxadiazol-2-amine or a pharmaceutically acceptable salt or solvate thereof for use in the treatment of chronic progressive multiple sclerosis.

The present invention further provides a method for treating chronic progressive multiple sclerosis in a patient (preferably a human), comprising administering to the patient a therapeutically effective amount of (−) 5-((((trans)-2-(4-(benzyloxy)phenyl)cyclopropyl)amino)methyl)-1,3,4-oxadiazol-2-amine or a pharmaceutically acceptable salt or solvate thereof.

The present invention further provides the use of (−) 5-((((trans)-2-(4-(benzyloxy)phenyl)cyclopropyl)amino)methyl)-1,3,4-oxadiazol-2-amine or a pharmaceutically acceptable salt or solvate thereof for the manufacture of a medicament for the treatment of chronic progressive multiple sclerosis.

The present invention further provides the use of (−) 5-((((trans)-2-(4-(benzyloxy)phenyl)cyclopropyl)amino)methyl)-1,3,4-oxadiazol-2-amine or a pharmaceutically acceptable salt or solvate thereof for the treatment of chronic progressive multiple sclerosis.

Preferably, the compound (−) 5-((((trans)-2-(4-(benzyloxy)phenyl)cyclopropyl)amino)methyl)-1,3,4-oxadiazol-2-amine (or a pharmaceutically acceptable salt or solvate thereof) is administered orally. Exemplary formulations which can be administered via peroral ingestion (or swallowing) are described in more detail further below.

As explained above, the present invention provides the compound (−) 5-((((trans)-2-(4-(benzyloxy)phenyl)cyclopropyl)amino)methyl)-1,3,4-oxadiazol-2-amine, or a pharmaceutically acceptable salt or solvate of said compound, for use in the treatment of multiple sclerosis. Accordingly, the invention relates to the compound (−) 5-((((trans)-2-(4-(benzyloxy)phenyl)cyclopropyl)amino)methyl)-1,3,4-oxadiazol-2-amine as a free base (in non-salt form) for use in the treatment of multiple sclerosis (e.g., chronic progressive multiple sclerosis) and, furthermore, the invention also relates to a pharmaceutically acceptable salt or solvate of (−) 5-((((trans)-2-(4-(benzyloxy)phenyl)cyclopropyl)amino)methyl)-1,3,4-oxadiazol-2-amine for use in the treatment of multiple sclerosis (e.g., chronic progressive multiple sclerosis).

As illustrated in the Examples, the compound (−) 5-((((trans)-2-(4-(benzyloxy)phenyl)cyclopropyl)amino)methyl)-1,3,4-oxadiazol-2-amine provides clear therapeutic effects in animal models of multiple sclerosis. In particular, Compound 1 has been tested using an Experimental Autoimmune Encephalomyelitis (EAE) model. EAE shows pathologic and clinical similarities to human MS and is widely used as a model system to test potential MS therapeutic agents. In particular, the murine EAE model as described in the Examples, using $MOG_{35-55}$ and C57BL/6 mice strain, is considered a validated preclinical model of the chronic progressive form of MS.

The effects of Compound 1 on chronic active EAE have been evaluated in a therapeutic regime, i.e. administering the compound after initiation of the disease symptoms. As illustrated in more detail in Example 3 and FIGS. 1, 2 and 4, treatment with Compound 1 greatly inhibited the development of EAE and reduced disease incidence and severity measured by daily mean clinical score. For example, in an EAE assay where Compound 1 was administered at 1 or 3 mg/kg p.o., while vehicle-treated mice developed moderate to severe signs of EAE and showed mortality due to severe paralysis, in the groups treated with Compound 1, 40-70% of the mice displayed mild symptoms and 30% of them almost completely recovered 40 days after disease onset. Compound 1 has been found to be effective in this MS model at doses as low as 0.05 mg/kg p.o., as shown in Example 3.3 and FIG. 2. Importantly, the protective effect of Compound 1 was maintained for a long period of time after cessation of the treatment.

It is remarkable that Compound 1 exhibits a fast onset of action against the progression of the disease, exhibiting beneficial effects on daily clinical score already shortly after start of the treatment, as shown e.g. in FIG. 1. Compound 1 may thus be beneficial to provide early relief of acute attacks of MS or rapidly progressing multiple sclerosis, and may provide an alternative to the standard treatment with high dose i.v. corticosteroids, especially in cases of hypersensitivity or allergy to corticosteroids.

Figure 5:
FIG. 5 shows the results of histopathological analysis of spinal cords isolated at the end of treatment (26 days after immunization) from animals treated with Compound 1 at 0.5 mg/kg p.o. or vehicle in the EAE assay as described in Example 4. The images shown correspond to transverse cervical (A) and lumbar (B) spinal cord sections selected at the peak of clinical disease, stained with Kluver-Barrera. Arrows point to areas of demyelination and inflammatory cell infiltration. The horizontal bar indicates a scale of 200 μm.
Figure 5:
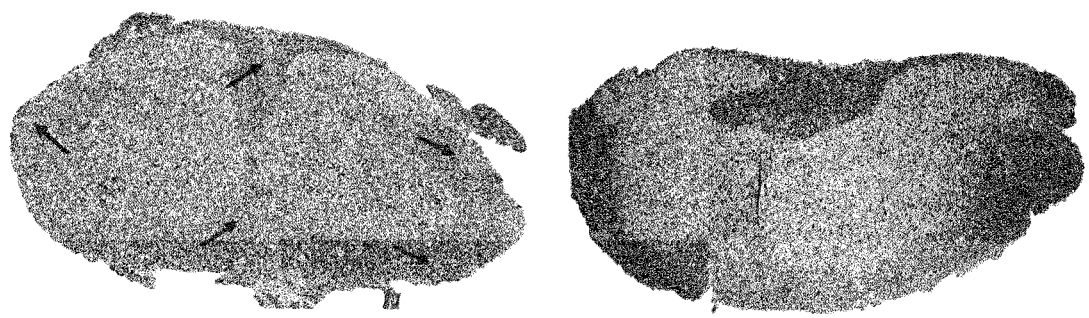
Figure 6:
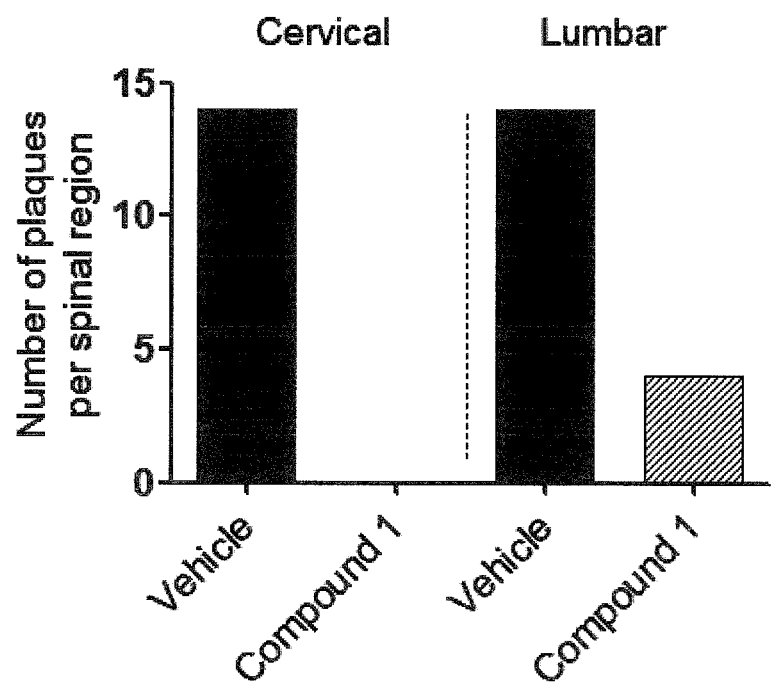
FIG. 6 shows the mean number of demyelination plaques in the lumbar and cervical regions corresponding to the spinal cords isolated in Example 4, demonstrating absent or greatly reduced demyelination in the cervical and lumbar spinal cord sections, respectively, of animals treated with Compound 1.

As illustrated in Example 4 and FIGS. 5 and 6, Compound 1 is useful to reduce infiltration of immune cells into the spinal cord as well as to reduce demyelination in the spinal cord, as shown in the EAE mice. Treatment with Compound 1 reduces egress of lymphocytes from immune tissues, as shown by a significant increase in the number of immune cells retained in the spleen and lymph nodes, as described in more detail in Example 4 and FIG. 7. Compound 1 also reduces proinflammatory cytokines such as IL-6 and IL-1beta and chemokines such as IP-10 and MCP-1 in the spinal cord (see FIG. 8). Cytokine IL-4 was significantly increased in spinal cords of Compound 1-treated animals, indicative of Th2 anti-inflammatory response (FIG. 8A).

Importantly, the therapeutic effects of Compound 1 in MS can be achieved at doses that do not produce clinically relevant effects on hematology or circulating lymphocyte counts, a common side effect in MS drugs, and/or without signs of gastro-intestinal toxicity. Accordingly, Compound 1 can be used to treat MS, including progressive MS, without producing clinically relevant effects on hematology or circulating lymphocyte counts.

The therapeutic effects of Compound 1 in the treatment of MS have been found to be unexpectedly outstanding, also when compared to the effects of other LSD1 inhibitors. Compound 1 is a cyclopropylamino-based irreversible LSD1 inhibitor. Using the EAE model of MS of Example 3.1, the effects of Compound 1 were compared to another cyclopropylamino-based irreversible LSD1 inhibitor, the compound designated ORY-LSD1, described in more detail in Example 1. Compound 1 exhibits an IC50 against LSD1 of 90 nM, while ORY-LSD1 has an IC50 against LSD1 of 10 nM, as described in more detail in Example 2. As the two compounds have different in vitro potencies against LSD1, ORY-LSD1 was tested in the EAE model of Example 3 at doses equivalent to those used for Compound 1 with respect to LSD1 inhibition in vivo. While ORY-LSD1 provided a clear tendency for improvement (FIG. 3), Compound 1 was considerably more effective than ORY-LSD1. Compound 1 is therefore a particularly suitable LSD1 inhibitor for use in treating multiple sclerosis.

Pharmaceutical Formulations

While it is possible that Compound 1 may be administered for use in therapy directly as such, it is typically administered in the form of a pharmaceutical composition, which comprises Compound 1 as active pharmaceutical ingredient together with one or more pharmaceutically acceptable excipients or carriers. Any reference to Compound 1 herein includes the compound as free base and any pharmaceutically acceptable salt or solvate thereof.

Compound 1 may be administered by any means that accomplish the intended purpose. Examples include administration by the oral, parenteral, intravenous, subcutaneous or topical routes.

For oral delivery, Compound 1 can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), and sweetening or flavoring agents (e.g., glucose, sucrose, saccharin, methyl salicylate, and peppermint). The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

Compound 1 can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and antioxidants can all be included. For example, useful components include sodium chloride, acetates, citrates or phosphates buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

For topical administration, Compound 1 can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al. (1988) *Ann. Rev. Med.* 39:221-229 which is incorporated herein by reference.

Subcutaneous implantation for sustained release of Compound 1 may also be a suitable route of administration. This entails surgical procedures for implanting an active compound in any suitable formulation into a subcutaneous space, e.g., beneath the anterior abdominal wall. See, e.g., Wilson et al. (1984) *J. Clin. Psych.* 45:242-247. Hydrogels can be used as a carrier for the sustained release of active compounds. Hydrogels are generally known in the art. They are typically made by crosslinking high molecular weight biocompatible polymers into a network, which swells in water to form a gel like material. Preferably, hydrogels are biodegradable or biosorbable. For purposes of this invention, hydrogels made of polyethylene glycols, collagen, or poly(glycolic-co-L-lactic acid) may be useful. See, e.g., Phillips et al. (1984) *J. Pharmaceut.* 73: 1718-1720.

Compound 1 can also be conjugated, to a water soluble non-immunogenic non-peptidic high molecular weight polymer to form a polymer conjugate. For example, Compound 1 can be covalently linked to polyethylene glycol to form a conjugate. Typically, such a conjugate exhibits improved solubility, stability, and reduced toxicity and immunogenicity. Thus, when administered to a patient, Compound 1 in the conjugate can have a longer half-life in the body, and exhibit better efficacy. See generally, Burnham (1994) *Am. J. Hosp. Pharm.* 15:210-218. PEGylated proteins are currently being used in protein replacement therapies and for other therapeutic uses. For example, PEGylated interferon (PEG-IN-TRON A®) is clinically used for treating Hepatitis B. PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). It is preferred that the covalent linkage between the polymer and the active compound and/or the polymer itself is hydrolytically degradable under physiological conditions. Such conjugates known as "prodrugs" can readily release the active compound inside the body. Controlled release of an active compound can also be achieved by incorporating the active ingredient into microcapsules, nanocapsules, or hydrogels generally known in the art. Other pharmaceutically acceptable prodrugs of Compound 1 include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters.

Liposomes can also be used as carriers for the active compound. Liposomes are micelles made of various lipids such as cholesterol, phospholipids, fatty acids, and derivatives thereof. Various modified lipids can also be used. Liposomes can reduce the toxicity of the active compounds, and increase their stability. Methods for preparing liposomal suspensions containing active ingredients therein are generally known in the art. See, e.g., U.S. Pat. No. 4,522,811; Prescott, Ed., Methods in Cell Biology, Volume XIV, Academic Press, New York, N.Y. (1976).

The pharmaceutical compositions, like oral and parenteral compositions, can be formulated in unit dosage forms for ease of administration and uniformity of dosage. As used herein, "unit dosage forms" refers to physically discrete units suitable as unitary dosages for administration to subjects, each unit containing a predetermined quantity of active ingredient calculated to produce the desired therapeutic effect, in association with one or more suitable pharmaceutical carriers.

In therapeutic applications, pharmaceutical compositions are to be administered in a manner appropriate to the disease to be treated, as determined by a person skilled in the medical arts. An appropriate dose and suitable duration and frequency of administration will be determined by such factors as the condition of the patient, the type and severity of the disease, the particular form of the active ingredient, the method of administration, among others. In general, an appropriate dose and administration regimen provides the pharmaceutical composition in an amount sufficient to provide therapeutic benefit, for example an improved clinical outcome, such as more frequent complete or partial remissions, or longer disease-free and/or overall survival, or lessening of symptoms severity, or any other objetively identifiable improvement as noted by the clinician. Effective doses may generally be assessed or extrapolated using experimental models like dose-response curves derived from in vitro or animal model test systems like the ones illustrated in the Examples. The pharmaceutical compositions of the invention can be included in a container, pack or dispenser together with instructions for administration.

Compound 1 is orally active and is effective in the treatment of MS when administered orally, as illustrated in Examples 3 and 4. Accordingly, it is preferred that Compound 1 is administered by the oral route for the treatment of MS.

Definitions

Unless defined otherwise, all technical and scientific terms used herein have the same meaning as commonly understood by one of ordinary skill in the art to which this invention pertains.

The following definitions apply throughout the present specification and claims, unless specifically indicated otherwise.

A "patient" or "subject" for the purposes of the present invention includes both humans and other animals, particularly mammals, and other organisms. Thus, the methods are applicable to both human therapy and veterinary applications. In a preferred aspect the subject or patient is a mammal, and in the most preferred aspect the subject or patient is human.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a patient and includes: (a) preventing a disease in a patient which may be predisposed/at risk of developing the disease; (b) inhibiting the disease, i.e. arresting its development; or (c) relieving the disease, i.e. causing regression of the disease. As used herein, the term "treating a disease" or "treatment of a disease" refers particularly to a slowing of or a reversal of the progress of the disease. Treating a disease includes treating a symptom and/or reducing the symptoms of the disease.

As used herein, the term "therapeutically effective amount" refers to the amount sufficient to produce a desired biological effect (e.g., a therapeutic effect) in a subject. Accordingly, a therapeutically effective amount of a compound may be an amount which is sufficient to treat a disease, and/or delay the onset or progression of a disease, and/or alleviate one or more symptoms of the disease, when administered to a subject suffering from or susceptible to that disease.

As used herein, a "pharmaceutically acceptable salt" is intended to mean a salt that retains the biological effectiveness of the free acids and bases of the specified compound and that is not biologically or otherwise undesirable. A compound may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of Compound 1 with a mineral or organic acid, such as hydrochlorides, hydrobromides, sulfates, pyrosulfates, bisulfates, sulfites, bisulfites, phosphates, monohydrophosphates, dihydrophosphates, metaphosphates, pyrophosphates, chlorides, bromides, iodides, nitrates, acetates, propionates, decanoates, caprylates, acrylates, formates, isobutyrates, caproates, heptanoates, propiolates, oxalates, malonates, succinates, suberates, sebacates, fumarates, maleates, butyne-1,4 dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycollates, tartrates, methanesulfonates, ethane-sulfonates, propanesulfonates, benzenesulfonates, toluenesulfonates, trifluoromethansulfonates, naphthalene-1-sulfonates, naphthalene-2-sulfonates, mandelates, pyruvates, stearates, ascorbates, or salicylates. When a compound carries an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands such as ammonia, alkylamines, hydroxyalkylamines, lysine, arginine, N-methylglucamine, procaine and the like. Pharmaceutically acceptable salts are well known in the art.

As used herein, a "pharmaceutically acceptable solvate" refers to a complex of variable stoichiometry formed by a solute and a pharmaceutically acceptable solvent such as water, ethanol and the like. A complex with water is known as a hydrate.

As used herein, a "pharmaceutically acceptable carrier" or "pharmaceutically acceptable excipient" refers to a non-API (API refers to Active Pharmaceutical Ingredient) substances such as disintegrators, binders, fillers, and lubricants used in formulating pharmaceutical products. They are generally safe for administering to humans according to established governmental standards, including those promulgated by the United States Food and Drug Administration and the European Medical Agency. Pharmaceutically acceptable carriers or excipients are well known to those skilled in the art.

EXAMPLES

The following examples illustrate various aspects of the invention. The examples should, of course, be understood to be merely illustrative of only certain embodiments of the invention and not to constitute limitations upon the scope of the invention. Results are also presented and described in the Figures and Figure legends.

Example 1: Materials

Compound 1 is the compound (−) 5-((((trans)-2-(4-(benzyloxy)phenyl)cyclopropyl)amino)methyl)-1,3,4-oxadiazol-2-amine, which can be obtained as disclosed in WO2012/013728.

ORY-LSD1 is the compound N-((1R,2S)-2-(2-fluorophenyl)cyclopropyl)piperidin-4-amine, which can be obtained as disclosed in WO2013/057320.

Example 2: In Vitro Biochemical Assays 2.1 LSD1

The inhibitory activity of a compound of interest against LSD1 can be tested using the method described below: Human recombinant LSD1 protein from BPS Bioscience Inc (catalog reference number 50100: human recombinant LSD1, GenBank accession no. NM_015013, amino acids 158-end with N-terminal GST tag, MW: 103 kDa) was used. In order to monitor LSD1 enzymatic activity and/or its inhibition rate by a test compound, di-methylated H3-K4 peptide (Anaspec) was chosen as a substrate. The demethylase activity was estimated, under aerobic conditions, by measuring the release of $H_2O_2$ produced during the catalytic process, using the Amplex® Red hydrogen peroxide/peroxidase assay kit (Invitrogen).

Briefly, a fixed amount of LSD1 was incubated on ice for 15 minutes, in the absence and/or in the presence of at least eight 3-fold serial dilutions of the respective inhibitor (e.g., from 0 to 75 μM, depending on the inhibitor strength). Tranylcypromine (Biomol International) was used as a control for inhibition. Within the experiment, each concentration of inhibitor was tested in duplicate. After leaving the enzyme interacting with the inhibitor, $K_M$ of di-methylated H3-K4 peptide was added to each reaction and the experiment was left for 30 minutes at 37° C. in the dark. The enzymatic reactions were set up in a 50 mM sodium phosphate, pH 7.4 buffer. At the end of the incubation, Amplex® Red reagent and horseradish peroxidase (HPR) solution were added to the reaction according to the recommendations provided by the supplier (Invitrogen), and left to incubate for 5 extra minutes at room temperature in the dark. A 1 μM $H_2O_2$ solution was used as a control of the kit efficiency. The conversion of the Amplex® Red reagent to resorufin due to the presence of $H_2O_2$ in the assay, was monitored by fluorescence (excitation at 540 nm, emission at 590 nm) using a microplate reader (Infinite 200, Tecan). Arbitrary units were used to measure level of $H_2O_2$ produced in the absence and/or in the presence of inhibitor. The maximum demethylase activity of LSD1 was obtained in the absence of inhibitor and corrected for background fluorescence in the absence of LSD1. The IC50 value of each inhibitor was calculated with GraphPad Prism Software.

2.2 Monoamine Oxidase A (MAO-A) and B (MAO-B)

LSD1 has a fair degree of structural similarity and amino acid identity/homology with the flavin-dependent amine oxidases monoamine oxidase A (MAO-A) and B (MAO-B). To determine the level of selectivity of a LSD1 inhibitor versus MAO-A and MAO-B, the inhibitory activity of a compound of interest against MAO-A and MAO-B can be tested using the method described below:

Human recombinant monoamine oxidase proteins MAO-A and MAO-B were purchased from Sigma Aldrich. MAOs catalyze the oxidative deamination of primary, secondary and tertiary amines. In order to monitor MAO enzymatic activities and/or their inhibition rate by inhibitor(s) of interest, a fluorescence-based (inhibitor)-screening assay was set up. 3-(2-Aminophenyl)-3-oxopropanamine (kynuramine dihydrobromide, Sigma Aldrich), a non fluorescent compound was chosen as a substrate. Kynuramine is a non-specific substrate for both MAO-A and MAO-B activities. While undergoing oxidative deamination by MAO activities, kynuramine is converted into 4-hydroxyquinoline (4-HQ), a resulting fluorescent product.

The monoamine oxidase activity was estimated by measuring the conversion of kynuramine into 4-hydroxyquinoline. Assays were conducted in 96-well black plates with clear bottom (Corning) in a final volume of 100 μL. The assay buffer was 100 mM HEPES, pH 7.5. Each experiment was performed in duplicate within the same experiment.

Briefly, a fixed amount of MAO was incubated on ice for 15 minutes in the reaction buffer, in the absence and/or in the presence of at least eight 3-fold serial dilutions each. Clorgyline and Deprenyl (Sigma Aldrich) was used as a control for specific inhibition of MAO-A and MAO-B respectively.

After leaving the enzyme(s) interacting with the inhibitor, $K_M$ of kynuramine was added to each reaction for MAO-B and MAO-A assay respectively, and the reaction was left for 1 hour at 37° C. in the dark. The oxidative deamination of the substrate was stopped by adding 50 μL of NaOH 2N. The conversion of kynuramine to 4-hydroxyquinoline, was monitored by fluorescence (excitation at 320 nm, emission at 360 nm) using a microplate reader (Infinite 200, Tecan). Arbitrary units were used to measure levels of fluorescence produced in the absence and/or in the presence of inhibitor.

The maximum of oxidative deamination activity was obtained by measuring the amount of 4-hydroxyquinoline formed from kynuramine deamination in the absence of inhibitor and corrected for background fluorescence in the absence of MAO enzymes. The IC50 values of each inhibitor were calculated with GraphPad Prism Software.

2.3 Results

Exemplary IC50 values against LSD1, MAO-A and MAO-B obtained using the above methods for Compound 1 and ORY-LSD1 are shown in the table below:

| Compound | LSD1 IC50 (μM) | MAO-B IC50 (μM) | MAO-A IC50 (μM) |
| --- | --- | --- | --- |
| Compound1 | 0.09 | 0.06 | 5.3 |
| ORY-LSD1 | 0.010 | >100 | >100 |

As can be seen from the above data, Compound 1 is a potent dual LSD1/MAO-B inhibitor. ORY-LSD1 is a potent LSD1 inhibitor with selectivity for LSD1 over MAO-A and MAO-B.

Example 3: Evaluation of the Efficacy of Compound 1 on Experimental Autoimmune Encephalomyelitis in Mice The Experimental Autoimmune Encephalomyelitis (EAE) model shows pathologic and clinical similarities to human multiple sclerosis (MS) and is widely used as a model for MS. In particular, the murine EAE model as described herein, using $MOG_{35-55}$ and C57BL/6 mice strain, is considered a validated preclinical model of the chronic progressive form of MS.

3.1 Method

To induce chronic EAE by active immunization, C57BL/6 mice were immunized s.c. with 100 µg of myelin oligodendrocyte glycoprotein $MOG_{35-55}$ emulsified in complete Freund's adjuvant (CFA) containing 4 mg/ml *Mycobacterium tuberculosis* H37 RA. Mice also received i.p. injections of 200 ng of pertussis toxin on days 0 and 2.

Treatment consisted in the oral administration of Compound 1 (at 1 mg/kg or 3 mg/kg) after the onset of the disease (day 12 postimmunization), once a day, for five consecutive days from day 12 to day 16 postimmunization and from day 19 to day 23 postimmunization. Control mice were orally treated with vehicle [2% v/v Tween-80+98% HPβCD (13% w/v)] following the same regime of administration as Compound 1. n=10 mice/group, with the exception of group treated with Compound 1 at 3 mg/kg where n=9.

Mice were scored daily for signs of EAE according to the following clinical scoring system: 0, no clinical signs; 0.5, partial loss of tail tonicity; 1, complete loss of tail tonicity; 2, flaccid tail and abnormal gait; 3, hind leg paralysis; 4, hind leg paralysis with hind body paresis; 5, hind and fore leg paralysis; and 6, death.

3.2 Results

Untreated control mice developed moderate (30% of animals reached a maximal clinical score of 1.5-3) to severe (70% of animals reached a maximal clinical score of 3.5-6) signs of EAE, and showed a mortality rate of 40% due to severe paralysis. Treatment with Compound 1 greatly inhibited the development of EAE and reduced disease incidence and severity measured by daily clinical score, as shown in FIG. 1. In the group treated with Compound 1, 40-70% of the mice displayed mild symptoms, and 30% almost completely recovered 40 days after disease onset. The protective effect of Compound 1 was maintained for a long-period of time after cessation of the treatment.

Based on the results obtained in this assay, Compound 1 is expected to be useful for the treatment of multiple sclerosis, including the chronic progressive form of multiple sclerosis.

3.3 Compound 1 is Effective at Doses as Low as 0.05 MG/KG

Figure 2:
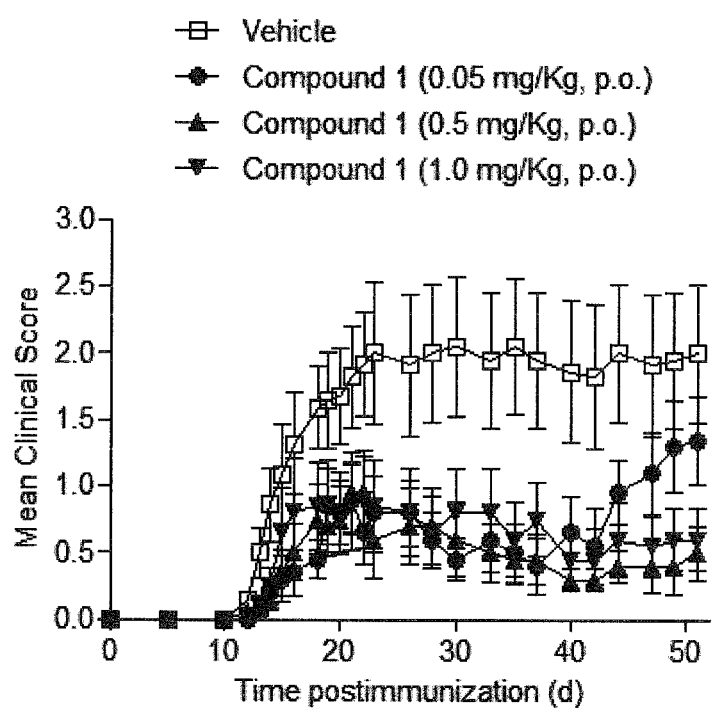
FIG. 2 shows the effects of Compound 1 at 1, 0.5 and 0.05 mg/kg p.o. in the EAE model as described in Example 3.3. Data represent the progression of the disease for each group measured as the mean clinical score (±SEM).

Using the same EAE assay protocol described in Example 3.1 above, Compound 1 was further tested at 1, 0.5 and 0.05 mg/kg p.o. starting at day 12 postimmunization, once a day, for five consecutive days from day 12 to day 16 postimmunization and from day 19 to day 23 postimmunization. Control mice were orally treated with vehicle [2% v/v Tween-80+98% HPβCD (13% w/v)] following the same regime of administration. Mice were scored daily for signs of EAE according to clinical scoring system described in Example 3.1. n=10 mice/group. As shown in FIG. 2, Compound 1 exhibited a clear effect on EAE, reducing clinical score at doses as low as 0.05 mg/kg p.o.

3.4 Comparison of the Effects of Compound 1 with Another LSD1 Inhibitor

Using the EAE model of Example 3.1, we tested another cyclopropylamino-based irreversible LSD1 inhibitor, ORY-LSD1, described in more detail in Example 1. ORY-LSD1 is a potent and selective inhibitor of LSD1. In order to be able to compare the results obtained with Compound 1 in Example 3.1 with ORY-LSD1 and as the two compounds have different in vitro potencies against LSD1 (see Example 2 for their IC50 values), ORY-LSD1 was administered in the EAE assay at doses chosen to be equivalent to those used for Compound 1 in Example 3.1 with respect to LSD1 inhibition in vivo. ORY-LSD1 was given at 0.06 and 0.180 mg/kg p.o. ORY-LSD1 and vehicle (same as in Example 3.1) were administered following the administration scheme as described in Example 3.1 (n=10 mice/group).

Figure 3:
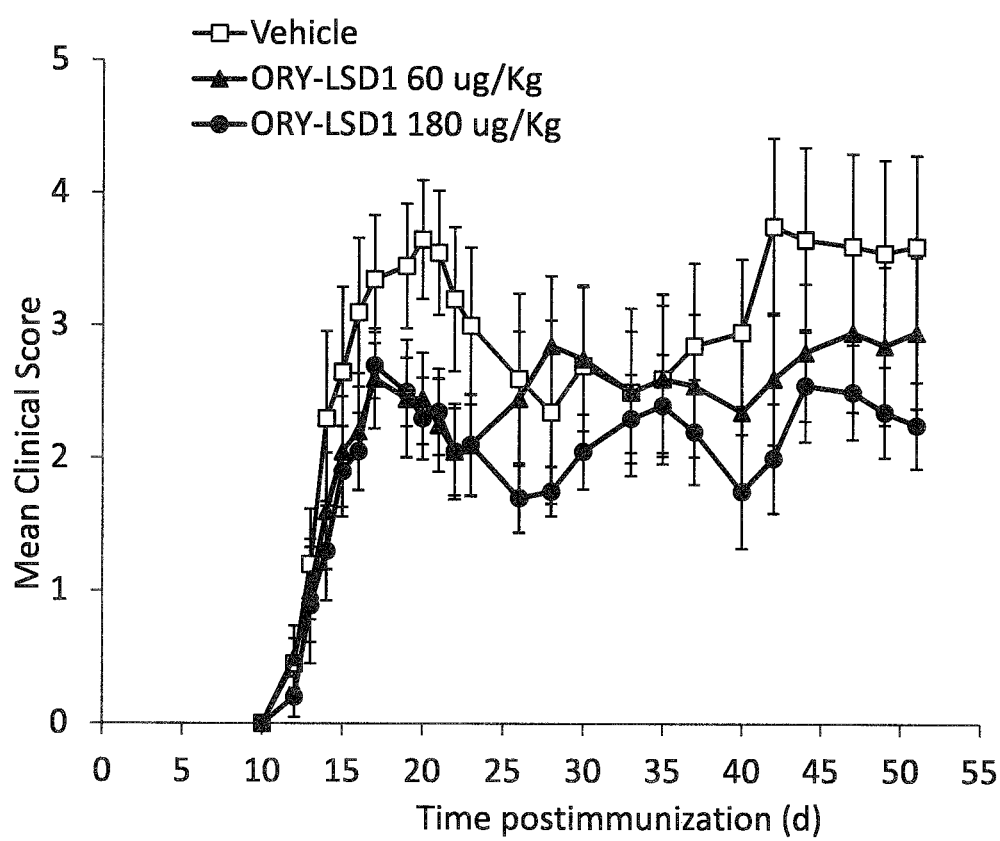
FIG. 3 shows the effects of the LSD1 inhibitor designated "ORY-LSD1" (as defined further in Example 1) at 0.06 and 0.180 mg/kg p.o in the EAE model as described in Example 3.4. Data represent the progression of the disease for each group measured as the mean clinical score (±SEM).

The results obtained with ORY-LSD1 are shown in FIG. 3. While ORY-LSD1 provided a clear tendency for improvement, ORY-LSD1 was considerably less effective than Compound 1. Compound 1 thus stands out as a particularly suitable compound for the treatment of multiple sclerosis.

Example 4: Further Characterisation of the Therapeutic Effects of Compound 1 on the EAE Model in Mice To further characterise the therapeutic effects of Compound 1 in the EAE model of Example 3, Compound 1 was further tested at 0.5 mg/kg p.o. and protein and histopathological analysis was performed. Treatment with Compound 1 followed the same scheme as described in Example 3.1, i.e. starting on day 12 postimmunization, once a day, for five consecutive days from day 12 to day 16 and from day 19 to day 23 postimmunization. Control mice were orally treated with vehicle [2% v/v Tween-80+98% HPβCD (13% w/v)] following the same regime of administration as Compound 1. Mice were scored daily for signs of EAE, using the scores described in Example 3.1. Animals were sacrificed on day 26 postimmunization and samples were collected and processed as described below. n=10 mice/group.

4.1 Methods

Tissue collection and cell isolation. On day 26 postimmunization, spleen, draining lymph nodes (DLNs: cervicals, inguinals and axillaries), and spinal cord were removed. Spinal segments of the cervical and lumbar regions were prepared separately and processed for protein extraction, and histopathological analysis. Single-cell suspensions were obtained from spleen or pooled lymph nodes, the samples were homogenized and total number of cells was quantified using Neubauer chamber.

Processing of samples for histopathological analysis. Cervical and lumbar spinal cord segments were divided and processed for inclusion and sectioning in paraffin. Spinal cord segments were immediately fixed with buffered 10% formalin for 48h, dehydrated and included in paraffin using standard techniques. Transversal sections (4-µm thickness) were stained with Luxol fast blue, cresyl violet, and hematoxylin following the Klüver-Barrera technique and were analyzed for the presence of areas of demyelination and cell infiltration using a light microscope (Leica, DM2000).

Protein extraction and cytokine/chemokine analysis. Proteins were extracted from cervical and lumbar segments of spinal cord by homogenization (50 mg tissue/all) in lysis buffer (50 mM Tris-HCl, pH 7.4, 0.5 mM DTT, and 10 µg/ml proteinase inhibitors PMSF, pepstatin, and leupeptin). Samples were centrifuged (20.000×g, 15 min, 4° C.) and the supernatants were assayed for protein concentration (using Bradford method) and for cytokine/chemokine contents by using specific sandwich ELISAs for IL-4, IL-6, IL-1beta, IP-10 and MCP-1, according to manufacturer's recommendations, using the following antibodies and recombinant proteins:

| | |
|---|---|
| IL-4 | Purified Rat Anti-Mouse IL-4. BD Pharmingen. 0.5 mg/ml. Ref: 554387. |
| | Recombinant Mouse IL-4. BD Pharmingen. 0.2 mg/ml. Ref: 550067. |
| | Biotin Rat Anti-Mouse IL-4. BD Pharmingen. 0.5 mg/ml. Ref: 554390 |
| IL-6 | Purified Rat Anti-Mouse IL-6. BD Pharmingen. 0.5 mg/ml. Ref: 554400. |
| | Recombinant Mouse IL-6. BD Pharmingen. 0.1 mg/ml. Ref: 554582. |
| | Biotin Rat Anti-Mouse IL-6. BD Pharmingen. 0.5 mg/ml. Ref: 554402. |
| IL-1beta | Purified Hamster Anti-Mouse IL-1Beta. BD Pharmingen. 0.5 mg/ml Ref: 550605. |
| | Recombinant Murine IL-1Beta. Peprotech. 0.1 mg/ml. Ref: 211-11B. |
| | Biotinylated Rabbit Anti-Murine IL-1Beta. Peprotech. 0.4 mg/ml. Ref: 500-P51Bt. |
| IP-10 | Anti-Murine IP-10 Antigen Affinity Purified Polyclonal Antibody. Peprotech. 0.5 mg/ml Ref: 500-P129. |
| | Recombinant Murine IP-10 (CXCL10). Peprotech. 0.1 mg/ml. Ref: 250-16. |
| | Biotinylated Antigen Affinity Purified Anti-Murine IP-10. Peprotech. Ref: 500-P129Bt. 0.5 mg/ml |
| MCP-1 | Anti-Murine JE/MCP-1. Antigen Affinity Purified Polyclonal Antibody. Peprotech. 0.5 mg/ml. Ref: 500-P113. |
| | Recombinant Murine JE/MCP-1 (CCL2). Peprotech. 0.1 mg/ml. Ref: 250-10. |
| | Biotinylated Anti-Murine JE Antigen Afinity Purified Polyclonal Antibody. Peprotech. 0.5 mg/ml. Ref: 500-P113Bt. |

Statistical Analysis: Cell number analysis in lymph nodes and spleen: statistical differences are indicated as ***p<0.001 vs vehicle using ANOVA test. Cytokine/chemokine level analysis: statistical differences are indicated as: *p<0.05, **p<0.005, using Mann-Whitney test; unpaired t-test was used for IP-10 level analysis.

4.2 Results

Figure 4:
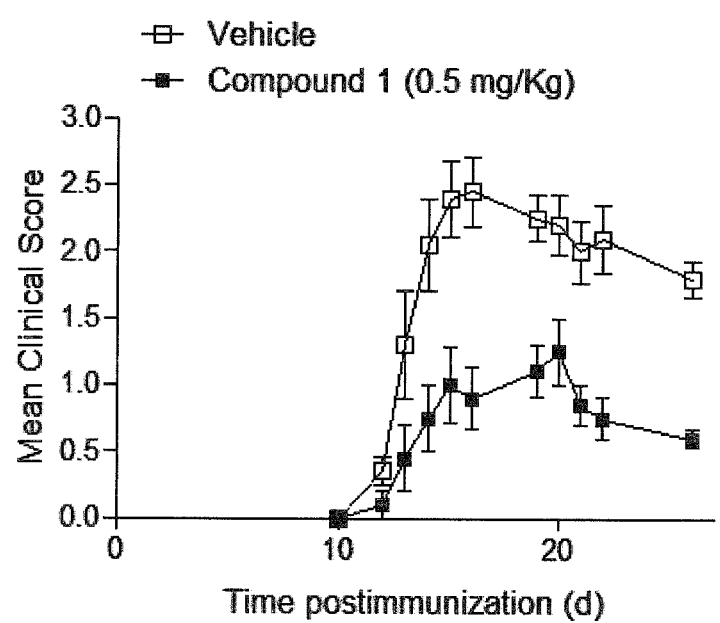
FIG. 4 shows the effects of Compound 1 at 0.5 mg/kg p.o. in the EAE assay as described in Example 4. Data represent the progression of the disease for each group measured as the mean clinical score (±SEM).

Treatment with Compound 1 at 0.5 mg/kg p.o., a dose well-tolerated by mice for long-term treatment, greatly inhibited the development of EAE and reduced disease incidence and severity, as measured by daily clinical score, as also shown in FIG. 4.

Compound 1 greatly reduced infiltration of inflammatory cells and demyelination in the spinal cord of EAE mice, as shown in FIG. 5. Arrows in said Figure show areas of demyelination and inflammatory cell infiltration. Multiple areas of demyelination and inflammatory cell infiltration were observed in the control (vehicle-treated animals) samples, both in the cervical and lumbar samples, whereas no inflammatory cell infiltration nor demyelination areas were observed in the Compound 1-treated samples. FIG. 6 shows the mean number of demyelination plaques in the lumbar and cervical regions of spinal cord of animals treated with Compound 1 or vehicle, demonstrating absent or greatly reduced demyelination in the cervical and lumbar sections of Compound 1-treated animals. These results, as also illustrated in FIGS. 5 and 6, show that Compound 1 reduces immune infiltration into the spinal cord and protects the spinal cord from demyelination in the EAE model of multiple sclerosis.

Figure 7:
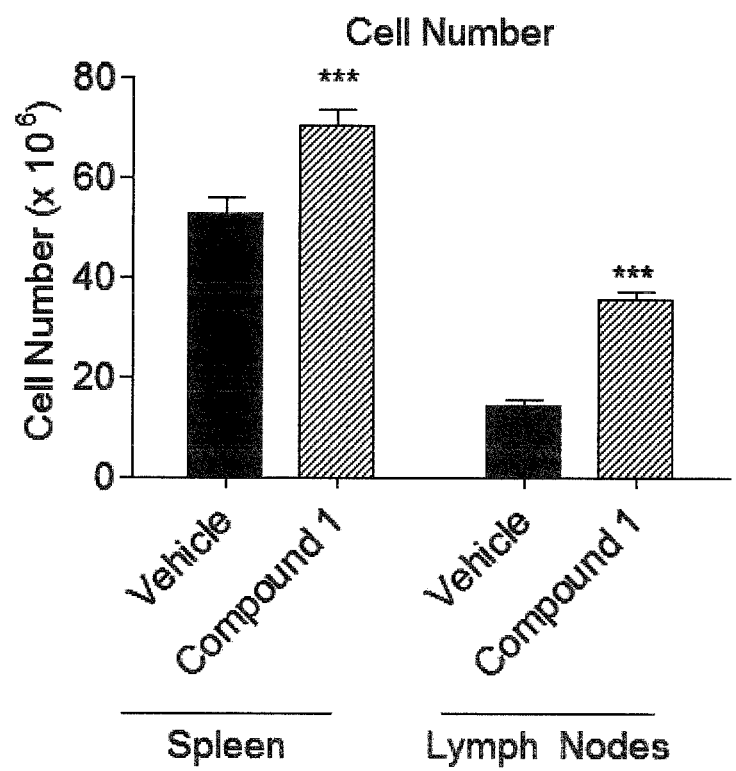
FIG. 7 shows the number of immune cells isolated from the spleen and lymph nodes of animals treated with Compound 1 at 0.5 mg/kg p.o. or vehicle according to Example 4, demonstrating a significant increase in the number of T cells retained in the spleen and lymph nodes of Compound 1-treated animals, indicating a reduced egress of lymphocytes from immune tissues.
Figure 8A:
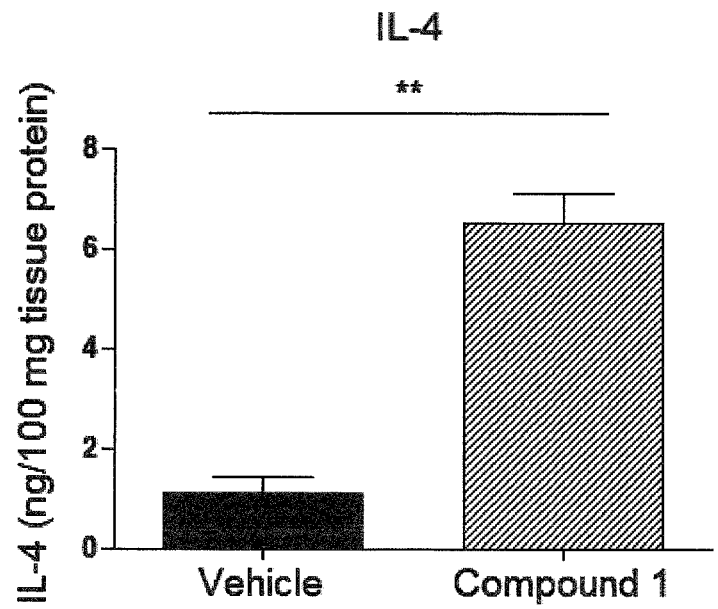
FIG. 8A: IL-4.
Figure 8B:
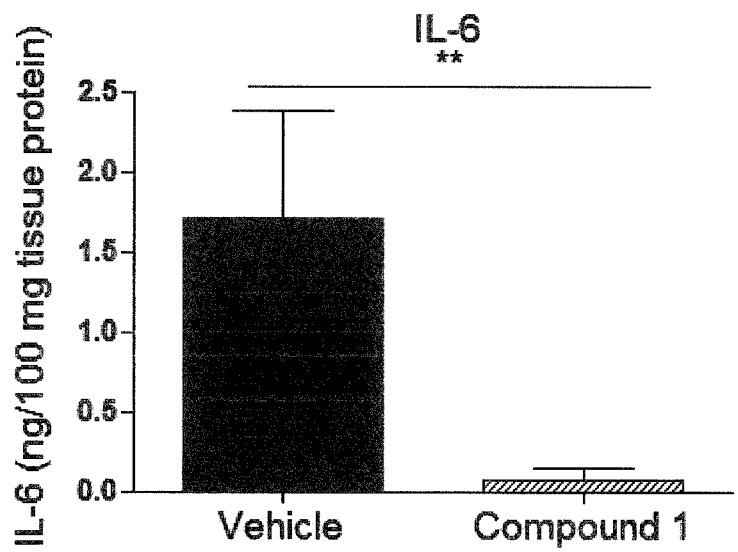
FIG. 8B: IL-6.
Figure 8C:
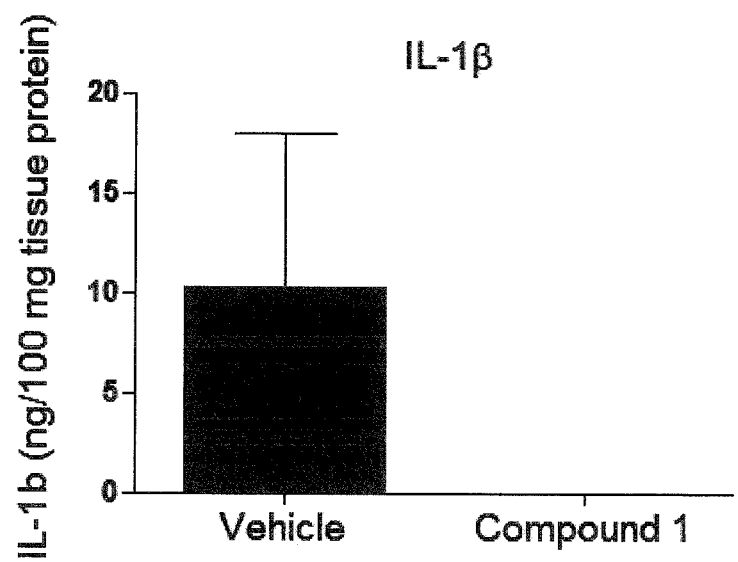
FIG. 8C: IL-1beta.
Figure 8D:
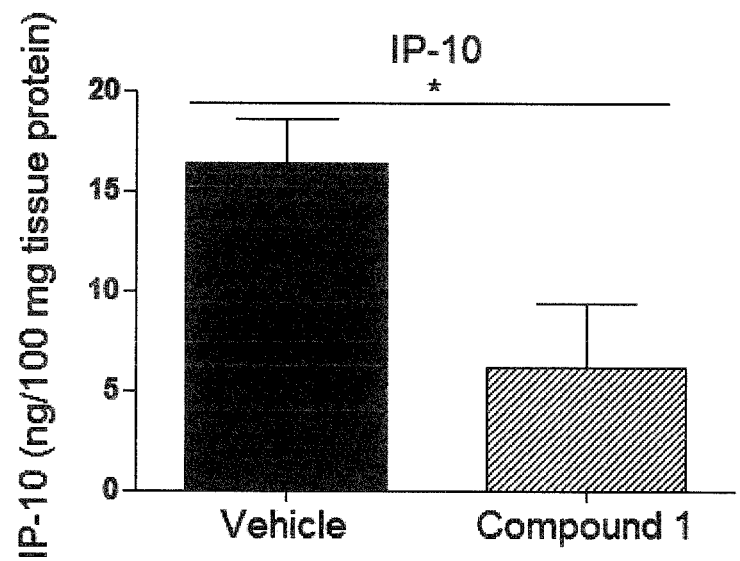
FIG. 8D: IP-10.
Figure 8E:
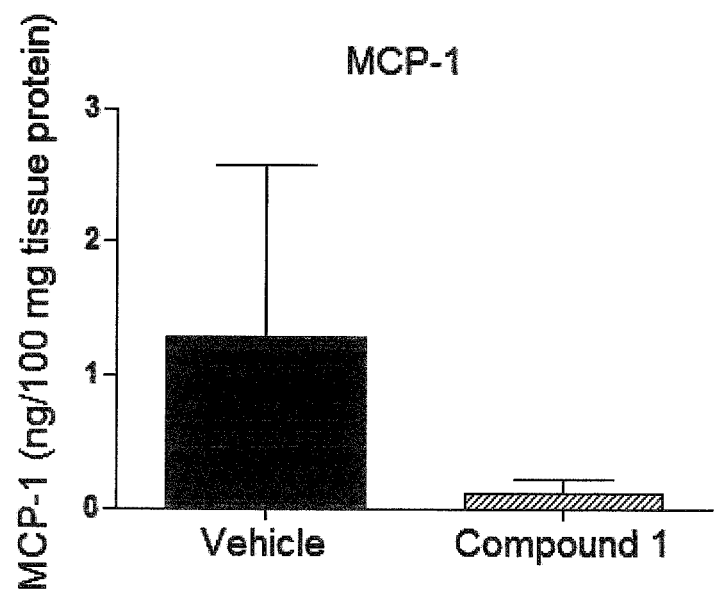
FIG. 8E: MCP-1. Levels are expressed as ng/100 mg of tissue protein.

As shown in FIG. 7, treatment with Compound 1 resulted in a significant increase in the number of immune cells retained in the spleen and lymph nodes of treated animals, indicating a reduced egress of lymphocytes from immune tissues. In addition, treatment with Compound 1 modulates inflammatory and auto-immune responses, as illustrated in FIGS. 8A to 8E. Antiinflammatory cytokine IL-4 was significantly increased in spinal cords of Compound 1-treated animals, indicative of Th2 anti-inflammatory response (FIG. 8A). Levels of pro-inflammatory cytokines IL-6 and IL-1 beta in spinal cord were reduced with Compound 1 treatment (FIGS. 8B and 8C). In addition, Compound 1 significantly reduced the levels of various chemokines in the target organ including IP-10 (FIG. 8D) and MCP-1 (FIG. 8E), which are involved in the recruitment of inflammatory and encephalitogenic Th1 cells to the spinal cord. These results further confirm that Compound 1 is particularly suitable as a therapeutic agent for the treatment of multiple sclerosis.

All publications, patents and patent applications cited herein are hereby incorporated herein by reference in their entireties.

The publications, patents and patent applications mentioned in the specification are provided solely for their disclosure prior to the filing date of the present application. Nothing herein is to be construed as an admission that they are prior art to the instant application.

While the invention has been described in connection with specific embodiments thereof, it will be understood that it is capable of further modifications and this application is intended to cover any variations, uses or adaptations of the invention following, in general, the principles of the invention and including such departures from the present disclosure as come within known or customary practice within the art to which the invention pertains and as may be applied to the essential features hereinbefore set forth and as follows in the appended claims.

The invention claimed is:

1. A method of treating multiple sclerosis, the method comprising administering, to a subject in need of treatment, a therapeutically effective amount of (−) 5-((((trans)-2-(4-(benzyloxy)phenyl) cyclopropyl)amino)methyl)-1,3,4-oxadiazol-2-amine or a pharmaceutically acceptable salt or solvate thereof.

2. The method of claim 1, wherein the compound is (−) 5-((((trans)-2-(4-(benzyloxy)phenyl)cyclopropyl)amino) methyl)-1,3,4-oxadiazol-2-amine or a pharmaceutically acceptable salt thereof.

3. The method of claim 1, wherein the compound is (−) 5-((((trans)-2-(4-(benzyloxy)phenyl)cyclopropyl)amino) methyl)-1,3,4-oxadiazol-2-amine.

4. The method of claim 1, wherein the multiple sclerosis is chronic progressive multiple sclerosis.

5. The method of claim 1, wherein the method comprises administering to the subject a therapeutically effective amount of (−) 5-((((trans)-2-(4-(benzyloxy)phenyl)cyclopropyl)amino)methyl)-1,3,4-oxadiazol-2-amine.

6. The method of claim 1, wherein the (−) 5-((((trans)-2-(4-(benzyloxy)phenyl)cyclopropyl)amino)methyl)-1,3,4- oxadiazol-2-amine or the pharmaceutically acceptable salt or solvate thereof is administered orally.

7. The method of claim 5, wherein the (−) 5-((((trans)-2-(4-(benzyloxy)phenyl)cyclopropyl)amino)methyl)-1,3,4-oxadiazol-2-amine is administered orally.

8. The method of claim 1, wherein the subject is a human.

9. A method of treating chronic progressive multiple sclerosis, the method comprising administering, to a subject in need of treatment, a therapeutically effective amount of (−) 5-((((trans)-2-(4-(benzyloxy)phenyl)cyclopropyl)amino)methyl)-1,3,4-oxadiazol-2-amine or a pharmaceutically acceptable salt or solvate thereof.

10. The method of claim 9, wherein the compound is (−) 5-((((trans)-2-(4-(benzyloxy)phenyl)cyclopropyl)amino)methyl)-1,3,4-oxadiazol-2-amine or a pharmaceutically acceptable salt thereof.

11. The method of claim 9, wherein the compound is (−) 5-((((trans)-2-(4-(benzyloxy)phenyl)cyclopropyl)amino)methyl)-1,3,4-oxadiazol-2-amine.

12. The method of claim 9, wherein the method comprises administering to the subject a therapeutically effective amount of (−) 5-((((trans)-2-(4-(benzyloxy)phenyl)cyclopropyl)amino)methyl)-1,3,4-oxadiazol-2-amine.

13. The method of claim 9, wherein the (−) 5-((((trans)-2-(4-(benzyloxy)phenyl)cyclopropyl)amino)methyl)-1,3,4-oxadiazol-2-amine or the pharmaceutically acceptable salt or solvate thereof is administered orally.

14. The method of claim 12, wherein the (−) 5-((((trans)-2-(4-(benzyloxy)phenyl)cyclopropyl)amino)methyl)-1,3,4-oxadiazol-2-amine is administered orally.

15. The method of claim 9, wherein the subject is a human.

16. The method of claim 3, wherein the subject is a human.

17. The method of claim 5, wherein the subject is a human.

18. The method of claim 11, wherein the subject is a human.

19. The method of claim 12, wherein the subject is a human.

* * * * *